US008975315B2

(12) United States Patent
Campbell et al.

(10) Patent No.: US 8,975,315 B2
(45) Date of Patent: Mar. 10, 2015

(54) STABILIZER COMPOSITION FOR HALOGEN-CONTAINING POLYMERS

(75) Inventors: Colin Campbell, Wigan Lancashire (GB); Bernhard Pelzl, Graz (AT); Anthony Stephen Butt, Almeria (ES)

(73) Assignee: Chemson Polymer-Additive AG, Arnoldstein (AT)

( * ) Notice: Subject to any disclaimer, the term of this patent is extended or adjusted under 35 U.S.C. 154(b) by 0 days.

(21) Appl. No.: 14/006,092

(22) PCT Filed: Mar. 21, 2012

(86) PCT No.: PCT/EP2012/055001
§ 371 (c)(1),
(2), (4) Date: Nov. 6, 2013

(87) PCT Pub. No.: WO2012/126948
PCT Pub. Date: Sep. 27, 2012

(65) Prior Publication Data
US 2014/0058020 A1    Feb. 27, 2014

Related U.S. Application Data

(60) Provisional application No. 61/454,611, filed on Mar. 21, 2011.

(51) Int. Cl.
| C08K 5/3492 | (2006.01) |
| C08L 27/00 | (2006.01) |
| C08L 27/04 | (2006.01) |
| C08L 27/06 | (2006.01) |
| C08L 27/08 | (2006.01) |
| C07D 251/34 | (2006.01) |
| C07D 251/38 | (2006.01) |

(52) U.S. Cl.
CPC .......... *C08K 5/34924* (2013.01); *C07D 251/34* (2013.01); *C07D 251/38* (2013.01)
USPC ............ 524/101; 252/405; 544/192; 544/221

(58) Field of Classification Search
USPC ................... 524/101; 252/405; 544/192, 221
See application file for complete search history.

(56) References Cited

U.S. PATENT DOCUMENTS

| 3,035,056 | A | 5/1962 | Symes |
| 4,039,485 | A | 8/1977 | Argabright et al. |
| 5,232,967 | A | 8/1993 | Worschech et al. |
| 5,312,941 | A | 5/1994 | Razvan et al. |
| 5,356,982 | A | 10/1994 | Razvan et al. |
| 5,519,077 | A | 5/1996 | Drewes et al. |
| 5,543,449 | A | 8/1996 | Drewes et al. |
| 8,772,382 | B2 | 7/2014 | Pelzl et al. |
| 2002/0103089 | A1 | 8/2002 | Fukushima et al. |
| 2003/0209696 | A1 | 11/2003 | Reith et al. |
| 2004/0204522 | A1 | 10/2004 | Austen et al. |
| 2009/0131564 | A1 | 5/2009 | Wehner et al. |
| 2011/0311744 | A1 | 12/2011 | Pelzl et al. |

FOREIGN PATENT DOCUMENTS

| AU | 2008286385 | | 2/2009 |
| CN | 101 798 428 A | | 8/2010 |
| DE | 41 06 404 C1 | | 7/1992 |
| DE | 41 06 411 C1 | | 7/1992 |
| DE | 42 04 887 A1 | | 8/1993 |
| DE | 10 11 8179 | | 10/2002 |
| DE | 10 2007 037 795 A1 | | 2/2009 |
| DE | 10 2008 058901 A1 | | 5/2010 |
| EP | 0 256 872 A2 | | 2/1988 |
| EP | 0 259 783 A2 | | 3/1988 |
| EP | 0 542 720 A1 | | 5/1993 |
| EP | 0 677 550 A2 | | 10/1995 |
| EP | 0 768 336 | | 4/1997 |
| EP | 1 343 838 | | 9/2003 |
| EP | 1 046 668 B1 | | 1/2004 |
| EP | 1 466 941 A2 | | 10/2004 |
| JP | 53 081592 A | | 7/1978 |
| JP | 60 040146 A | | 3/1985 |
| JP | 05 179090 | | 7/1993 |
| JP | 05 295198 | | 11/1993 |
| JP | 07 062181 | | 3/1995 |
| JP | 11 129409 | | 5/1999 |
| JP | 2001 200374 A | | 7/2001 |
| JP | 2002 080876 A | | 3/2002 |
| SU | 440382 A | * | 2/1975 |
| SU | 531806 A | * | 11/1976 |
| WO | WO 02/48249 A2 | | 6/2002 |
| WO | WO 2006/136191 A1 | | 12/2006 |
| WO | WO 2010/060966 A1 | | 6/2010 |

(Continued)

OTHER PUBLICATIONS

SU 531806 A, Nov. 1976, Derwent Ab.*
SU 440382 A, Feb. 1975, Derwent Ab.*
Chiron-Charrier, et al. 1993. Application of the study of reactivity of alkaline salts of isocyanuric acid to the synthesis of mono and trisubstituted isocyanurates. Synthetic Communications, Taylor & Francis Group, Philadelphia, PA. vol. 23, No. 19, pp. 2659-2672.
Gächter, R., & Müller, H. 1989. *Kunststoffadditive*. Carl Hanser Verlag, 3rd Ed., pp. 478-488.
S. Cockett et al. Nov. 2005. Photoblueing von PVC-Profilen. Gummi Fasern Kunststoffe, vol. 58, pp. 704-710.
International Search Report mailed Mar. 31, 2010 in PCT Application No. PCT/EP2009/065926, filed Nov. 26, 2009, 4 pages.
International Preliminary Report on Patentability dated Mar. 25, 2011 in PCT Application No. PCT/EP2009/065926, filed Nov. 26, 2009, 5 pages.

(Continued)

*Primary Examiner* — Satya Sastri
(74) *Attorney, Agent, or Firm* — Knobbe Martens Olson & Bear LLP

(57) ABSTRACT

The present invention relates to a stabilizer composition for halogen-containing polymers and polymer mixtures, comprising at least one metal salt of isocyanuric acid, isothiocyanuric acid or a derivative thereof, to a process for the preparation thereof, the thus produced stabilizer compositions, polymer compositions comprising the stabilizer compositions, and to methods of using the stabilizer compositions.

20 Claims, No Drawings

(56) References Cited

FOREIGN PATENT DOCUMENTS

WO     WO 2012/126948 A1    9/2012
WO     WO 2012/140054 A1    10/2012

OTHER PUBLICATIONS

International Search Report mailed May 25, 2012 for International Application No. PCT/EP2012/055001 filed Mar. 21, 2012, 4 pages.
International Preliminary Report on Patentability dated Sep. 24, 2012 in PCT Application No. PCT/EP2012/055001, filed Mar. 21, 2012, 6 pages.
International Search Report mailed Jun. 5, 2012 for International Application No. PCT/EP2012/056540 filed Apr. 4, 2012, 3 pages.
Preliminary Amendment filed May 25, 2011 for U.S. Appl. No. 13/131,232, filed Sep. 8, 2011, 9 pages.
Restriction Requirement mailed Nov. 26, 2012 for U.S. Appl. No. 13/131,232, filed Sep. 8, 2011, 8 pages.
Response to Restriction Requirement filed Dec. 17, 2012 for U.S. Appl. No. 13/131,232, filed Sep. 8, 2011, 9 pages.
Office Action mailed Mar. 28, 2013 for U.S. Appl. No. 13/131,232, filed Sep. 8, 2011, 8 pages.
Reply to Office Action filed Sep. 27, 2013 for U.S. Appl. No. 13/131,232, filed Sep. 8, 2011, 13 pages.
Notice of Allowance mailed Mar. 3, 2014 for U.S. Appl. No. 13/131,232, filed Sep. 8, 2011, 12 pages.
Preliminary Amendment filed Sep. 18, 2013 for Application No. 14/110,096, filed Oct. 4, 2013, 8 pages.
Unpublished Experimental Results, Sep. 20, 2013.

* cited by examiner

STABILIZER COMPOSITION FOR HALOGEN-CONTAINING POLYMERS

CROSS-REFERENCE TO RELATED APPLICATIONS

This application is the U.S. National Phase of Application No. PCT/EP2012/055001 entitled "STABILIZER COMPOSITION FOR HALOGEN-CONTAINING POLYMERS" filed Mar. 21, 2012 and published in English on Sep. 27, 2012 as WO 2012/126948 which claims the benefit of priority of U.S. provisional application No. 61/454,611 filed Mar. 21, 2011, entitled "Isocyanuric acid salts for the stabilization of halogenated thermoplastics". The entire content of said application filed on Mar. 21, 2011 is incorporated herein by reference for all purposes, including an incorporation of any element or part of the description, claims or drawings not contained herein and referred to in Rule 20.5(a) of the PCT, pursuant to Rule 4.18 of the PCT.

FIELD OF THE INVENTION

The present invention relates to a stabilizer composition for halogen-containing polymers and polymer mixtures, comprising at least one metal salt of isocyanuric acid, isothiocyanuric acid or a derivative thereof, to a process for the preparation thereof, the thus produced stabilizer compositions, polymer compositions comprising the stabilizer compositions, and to methods of using the stabilizer compositions.

BACKGROUND

Halogen-containing polymers or plastics or molded articles produced therefrom tend to undergo substantial changes during their production process and under environmental influences. For example, they tend to decompose and degrade under the influence of heat and/or light. The degradation of such halogen-containing polymers, in particular PVC, produces halogenic acid (in case of PVC hydrochloric acid), which is eliminated from the polymer strands, resulting in a discolored, unsaturated plastic having chromophoric polyene sequences.

To avoid these undesirable changes, it is common practice in the art to add stabilizers to these polymers that at least partially prevent decomposition and/or discoloration first during the production process and then later on during the lifetime of the product. In the past, toxic heavy metal-containing compounds, such as lead, barium or cadmium containing compounds, have been used as stabilizers. However, due to the toxicity and environmental concerns, in the recent years, attempts have been made to find alternative stabilizers. Today a growing number of heavy metal-free stabilizer compositions is available, including among others, hydrotalcites, perchlorates, alkaline earth metal oxides, hydroxides and carboxylates, etc. Other known stabilizers include nitrogen-containing compounds, such as aminouracils and isocyanurates.

THEIC (Tris-hydroxyethylene-isocyanurate), for example, is well known and well used in stabilization of halogenated thermoplastics, especially PVC. The mode of action is not completely elucidated, but it is hypothesized that THEIC as a polyol complexes Zinc cations and thus delays the formation of the Lewis acid $[ZnCl_4]^{2-}$ which catalyzes the degradation of PVC-polymer chains.

Despite numerous stabilizer compositions being known and available, there is still need for alternative stabilizers with improved properties, for example with respect to initial coloring and color stability, while being environmentally safe and non-toxic.

SUMMARY OF THE INVENTION

One object of the present invention was to meet this need by providing a stabilizer composition for halogenated polymers that satisfies the needs identified above. A further object of the invention was to provide a method for its production. Another object of the invention was to provide a polymer composition that comprises such a stabilizer composition and methods of stabilizing halogen-containing polymers by use of the inventive stabilizer compositions as well as providing molded polymer products that include these compositions.

The objects of the invention are achieved by the compositions, methods and uses, as described below.

In a first aspect, the present invention is directed to a stabilizer composition for halogen-containing polymers, comprising at least one metal salt of a compound of formula I or a tautomer or stereoisomer thereof:

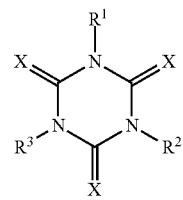

Formula I wherein
$R^1$, $R^2$ and $R^3$ are independently selected from the group consisting of hydrogen, halogen, hydroxy, cyano, amino, optionally substituted alkyl, optionally substituted alkenyl, optionally substituted alkynyl, optionally substituted cycloalkyl, optionally substituted heterocyclyl, optionally substituted aryl, optionally substituted heteroaryl, optionally substituted alkoxy, and —C(O)R;
R is selected from the group consisting of hydrogen, hydroxy, alkyl, alkenyl, alkynyl, aryl, heteroaryl, cycloalkyl, heterocyclyl, and amino; and
each X is independently oxygen (O) or sulphur (S).

In various embodiments, the metal salt of the compound of formula I is a compound of formula II:

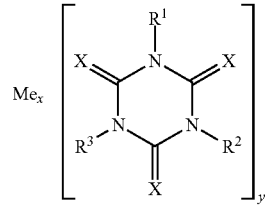

Formula II wherein
$R^1$, $R^2$, $R^3$ and X are defined as above, Me is a metal ion, x is an integer from 1 to 6, y is an integer from 1 to 4. In various embodiments of such compounds, the metal ion is positively charged and has a charge m+, with no being an integer from 1 to 4, preferably from 1 to 3, and the triazine moiety is negatively charged and has a charge n-, with n being an integer from 1 to 6. In various embodiments, x and y are selected such that the net charge of the salt is zero. The compound may be present in form of a solid salt and, in solution, may dissociate to the respective cation(s) and anion(s).

In various embodiments of the present invention, one, two or all three of $R^1$, $R^2$ and $R^3$ are hydrogen, hydroxyethyl, propenyl, or 1,2-epoxypropan-3yl. In various embodiments, X is O.

In various embodiments, the metal salt includes an alkali metal, alkaline earth metal, aluminum, lead and/or zinc. The alkali metal or alkaline earth metal may, for example, be selected from the group consisting of sodium, potassium, magnesium and calcium. Hence, in the compound of formula II, each metal ion Me can, in various embodiments, independently be selected from the group consisting of an alkali metal, alkaline earth metal, aluminum, lead and zinc. Again, the alkali metal or alkaline earth metal may, for example, be selected from the group consisting of sodium, potassium, magnesium and calcium.

In various embodiments of the invention, the metal salt of the compound of formula I is trisodium trishydroxyethylene isocyanurate, trisodium trispropylene isocyanurate, trisodium trispropylene oxide isocyanurate or trisodium isocyanurate.

In various embodiments of the invention, the stabilizer composition further comprises one or more additional components. Such components may be selected from the group consisting of primary stabilizers, co-stabilizers, zeolites, antioxidants, fillers, plasticizers, dyestuffs, pigments, antistatic agents, surfactants, blowing agents, impact modifiers, UV stabilizers, lubricants, processing agents and other auxiliaries.

In various embodiments, the additional (co-)stabilizers are selected from the group consisting of 1,3-diketone compounds, polyols, metal salts, natural or synthetic minerals, amino acid derivatives, organic esters of phosphorous acid, epoxy compounds, salts of halogen-containing oxy acids and amino alcohols.

In a second aspect, the present invention relates to a process of preparing a stabilizer composition according to the invention, the process comprising: reacting a compound of formula I, as defined above, with a metal hydroxide or metal oxide in the presence of catalytic amounts of water.

In specific embodiments of the process, the metal hydroxide or metal oxide is selected from the group consisting of alkali metal hydroxides, alkaline earth metal hydroxides, alkaline earth metal oxides, aluminum hydroxide, lead hydroxide, lead oxide, zinc oxide, and zinc hydroxide. Also contemplated is the use of more than one metal hydroxide or oxide, for example combinations of the afore-mentioned hydroxides and/or oxides.

The process of the invention can further comprise the step of drying the reaction product and/or the step of adding one or more additional components selected from the group consisting of primary stabilizers, co-stabilizers, zeolites, antioxidants, fillers, plasticizers, dyestuffs, pigments, antistatic agents, surfactants, blowing agents, impact modifiers, UV stabilizers, lubricants, processing agents and other auxiliaries to said composition after the reaction step.

In another aspect, the invention is directed to the stabilizer compositions obtainable according to the process of the invention.

In a still further aspect, the invention relates to a polymer composition comprising a halogen-containing polymer and a stabilizer composition according to the invention. The halogen-containing polymer may be a thermoplastic, such as polyvinylchloride (PVC).

The polymer composition may, in various embodiments, comprise one or more additional components selected from the group consisting of primary stabilizers, co-stabilizers, zeolites, antioxidants, fillers, plasticizers, dyestuffs, pigments, antistatic agents, surfactants, blowing agents, impact modifiers, UV stabilizers, lubricants, processing agents and other auxiliaries.

In various embodiments, the amount of stabilizer composition in the polymer composition can range from about 0.1 to about 20 per hundred halogen-containing polymer resin (phr).

In another aspect, the invention features a molded article comprising or consisting of the polymer composition of the invention.

The invention further relates to a method for the stabilization of halogen-containing polymers, comprising contacting the halogen-containing polymer with a stabilizer composition according to the invention. The contacting may include blending and/or mixing. In certain embodiments, the halogen-containing polymer is polyvinylchloride.

In another aspect, the invention is directed to the use of the stabilizer composition of the invention for stabilizing halogen-containing polymers, in particular PVC.

DETAILED DESCRIPTION

The present invention is based on the finding that when converting isocyanuric acid or derivatives thereof with bases, the resulting products are able to further increase the dynamic stability of PVC-melts compared to the free acids. Dynamic stability is an important quality when processing PVC as the melt has to bear up against heat and friction for some time.

The present invention therefore concerns stabilizer compositions for stabilizing halogen-containing polymers comprising an isocyanuric acid metal salt, an isothiocyanuric acid metal salt, a metal salt of an isocanuric acid or isothiocanuric acid derivative, or combinations thereof.

Examples of halogen-containing polymers can be thermoplastic halogen-containing polymers, for example, without being limited thereto, polyvinyl chloride (PVC), polyvinylidene chloride, chlorinated or chlorosulfonated polyethylene, chlorinated poly-propylene or chlorinated ethylene/vinyl acetate copolymer or similar compounds. Polymers of the PVC type, i.e. vinyl chloride homopolymers and copolymers of vinyl chloride with other monomers, are preferred.

The iso(thio)cyanuric acid or derivative may be a compound of formula I or a tautomer or stereoisomer thereof:

Formula I

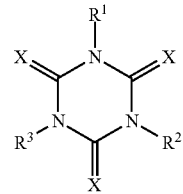

wherein
$R^1$, $R^2$ and $R^3$ are independently selected from the group consisting of hydrogen, halogen, hydroxy, cyano, optionally substituted alkyl, optionally substituted alkenyl, optionally substituted alkynyl, optionally substituted cycloalkyl, optionally substituted heterocyclyl, optionally substituted aryl, optionally substituted heteroaryl, optionally substituted alkoxy, —N(R)$_2$ and —C(O)R;
each R is independently selected from the group consisting of hydrogen, hydroxy, alkyl, alkenyl, alkynyl, aryl, heteroaryl, cycloalkyl, heterocyclyl, and amino; and
each X is independently oxygen (O) or sulphur (S).

As used herein, a "stabilizer composition" is to be understood as being a composition that can be used for stabilizing halogen-containing polymers. For achieving such stabilizing effect, a stabilizer composition according to the invention is mixed with a halogen-containing polymer to be stabilized and then the polymer processed. It is equally possible, however, for a stabilizer composition according to the invention to be mixed with the halogen-containing polymer during processing.

The term "alkyl", as used herein, relates to completely saturated aliphatic, linear or branched hydrocarbons. In particular embodiments, an alkyl contains 1 to 20 carbon atoms. A numerical range of from, for example, 1 to 20 means that, for example, $C_1$-$C_{20}$ alkyl relates to an alkyl group which contains 1, 2, 3, 4, 5, 6, 7, 8, 9, 10, 11, 12, 13, 14, 15, 16, 17, 18, 19 or 20 carbon atoms. The alkyl group can be a lower alkyl group and have 1-6 or 1-4 carbon atoms. The alkyl group can be optionally substituted, with the substituents as defined below. Examples of alkyl compounds include, but are not limited thereto, methyl, ethyl, n-propyl, isopropyl, n-butyl, isobutyl, sec-butyl, tert-butyl, pentyl, hexyl, heptyl, octyl and the like.

The term "alkenyl", as used herein, relates to aliphatic hydrocarbons having one or more double bonds. In particular embodiments an alkenyl contains 2 to 20 carbon atoms. The alkenyl group can also be a lower alkenyl and comprise 2 to 6 or 2 to 4 carbon atoms. The alkenyl group can be optionally substituted. Examples of alkenyl compounds include, but are not limited thereto, ethenyl, propenyl, 1,4-butadienyl and the like.

The term "alkynyl", as used herein, relates to aliphatic hydrocarbons having one or more triple bonds. In particular embodiments an alkynyl contains 2 to 20 carbon atoms. The alkynyl group can also be a lower alkenyl and comprise 2 to 6 or 2 to 4 carbon atoms. The alkynyl group can be optionally substituted. Examples of alkynyl compounds include, but are not limited thereto, ethynyl, propynyl and the like The term "alkoxy", as used herein, relates to aliphatic hydrocarbons having an —O-alkyl unit. In such units, the alkyl moiety is defined as described above. In particular embodiments an alkoxy contains 1 to 6 carbon atoms, i.e. 1, 2, 3, 4, 5 or 6 carbon atoms. The alkoxy group can be optionally substituted. Examples of alkoxy compounds include, but are not limited thereto, methoxy, ethoxy, propoxy, tert-butoxy and the like.

The term "cycloalkyl", as used herein, relates to cyclic saturated hydrocarbons. In particular embodiments a cycloalkyl contains 5 to 20 carbon atoms, i.e. 5, 6, 7, 8, 9, 10, 11, 12, 13, 14, 15, 16, 17, 18, 19 or 20 carbon atoms. The cycloalkyl group can be optionally substituted. If substituted with an alkyl group, the cycloalkyl group may be an alkylcycloalkyl group. Examples of cycloalkyl compounds include, but are not limited thereto, cyclopentane, cyclohexane, cycloheptane, cyclooctane and the like.

The term "alkylcycloalkyl", as used herein, relates to cyclic saturated hydrocarbons which are bonded to the core ring structure via an alkyl group. In particular embodiments an alkylcycloalkyl contains 4 to 20 carbon atoms. The alkylcycloalkyl group can be optionally substituted. Examples of alkylcycloalkyl compounds include, without being limited thereto, glycidyl and the like.

The terms "heterocyclyl" and "heterocycloalkyl", as interchangeably used herein, relate to cyclic saturated hydrocarbons that comprise one or more heteroatoms. The heteroatoms may be selected from oxygen, nitrogen, phosphorus and sulfur, but is not limited thereto. In particular embodiments a heterocycloalkyl contains 2 to 5 carbon atoms and 1 to 3 heteroatoms. The heterocycloalkyl group can be optionally substituted. The heterocycloalkyl group can be substituted by an alkyl group to form an alkylheterocycloalkyl group. One exemplary group is 2,3-epoxypropanyl.

The term "aryl", as used herein, relates to an aromatic ring in which each ring atom is a carbon atom. Aryl rings can be built up from five, six, seven, eight, nine, ten or more carbon atoms. For example, aryl compounds can have up to 15 carbon atoms. The aryl group can be optionally substituted. Examples of aryl compounds include, but are not limited thereto, cyclopentadienyl, phenyl, and the like.

The term "heteroaryl", as used herein, relates to an aromatic heterocycle, wherein the heteroaryl rings can be built up from 5, 6, 7, 8, 9 or more atoms, at least ring atom being a hetero atom. The at least one hetero atom can be chosen from oxygen, nitrogen, sulfur and phosphorus, but is not limited thereto. The heteroaryl group can be optionally substituted. Examples of heteroaryl compounds include, but are not limited thereto, furan, pyridine, thiophene and the like.

"Halogen", as used herein, relates to fluorine, chloride, bromine and iodine.

"Hydroxy", as used herein, relates to the group —OH.

"Cyano", as used herein, relates to the group —CN.

The term "optionally substituted" relates to a group in which one or more hydrogen atoms are replaced by a substituent. The substituent can be selected from the group consisting of alkyl, alkenyl, alkynyl, alkoxy, cycloalkyl, heterocycloalkyl, aryl, heteroaryl, OH, CN, halogen, nitro, carboxy, sulfonyl, phosphoryl, and amino, but is not limited thereto. The substituent groups can be defined as described above.

"Metal salt", as used herein, relates to adducts formed by combining an isocyanuric acid or derivative thereof or an isothiocyanuric acid or derivative thereof with this acid or derivative thereof optionally being a compound of formula I, with a metal-containing base, in particular a metal oxide or metal hydroxide. The iso(thio)cyanuric acid derivatives preferably comprise one or more acidic groups that are proton donors, including hydroxy, carboxy, sulfonic acid and phosphonic acid groups. The term as used herein includes the respective hydrates and solvates of the salts, including all salt forms that contain one or more crystal water molecules.

"Tautomer", as used herein, relates to specific structural isomers that readily interconvert by the so-called tautomerization, commonly resulting in the formal migration of a hydrogen atom or proton, accompanied by a switch of a single bond and adjacent double bond. By way of example, a tautomer of isocyanuric acid may include cyanuric acid.

"Stereoisomer", as used herein, refers to isomeric molecules that have the same molecular formula and sequence of bonded atoms, but that differ in the three-dimensional orientations of their atoms in space.

In various embodiments, the metal salt of the compound of formula I is a compound of formula

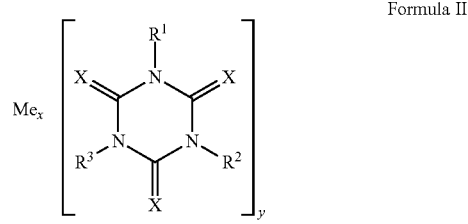

Formula II wherein
$R^1$, $R^2$, $R^3$ and X are defined as above, Me is a metal ion, x is an integer from 1 to 6, y is an integer from 1 to 4. In various embodiments of such compounds, the metal ion is positively charged and has a charge m+, with m being an integer from 1 to 4, preferably from 1 to 3, and the triazine moiety is negatively charged and has a charge n−, with n being an integer from 1 to 6. In various embodiments, x and y are selected such that the net charge of the salt is zero. The compound may be present in form of a solid salt and, in solution, may dissociate to the respective cation(s) and anion(s).

In various embodiments of the present invention, $R^1$ to $R^3$ are independently hydrogen, hydroxyalkyl, such as hydroxyethyl, epoxyalkyl, or alkenyl. Exemplary hydroxyalkyl groups are hydroxymethyl, hydroxyethyl and hydroxypropyl. Exemplary epoxyalkyl groups are 2,3-epoxypropanol, 3,4-epoxybutanol and the like. Exemplary alkenyl groups are ethenyl and propenyl.

In various embodiments of the invention $R^1$, $R^2$ and $R^3$ are the same group. In such embodiments, $R^1$-$R^3$ may be selected from hydrogen, hydroxyethyl, 2,3-epoxypropyl and 2-propenyl. In one embodiment, when $R^1$-$R^3$ are hydrogen, the compound of formula I may be cyanuric acid, i.e. the tautomer of isocyanuric acid. In one preferred embodiment, the compound of formula I is trishydroxyethyl isocyanuric acid (THEIC).

The metal salts of the compounds of formula I can be salts with any metal, but preferably the metal is selected from the group consisting of an alkali metal, alkaline earth metal, aluminum, lead or zinc. The alkali metal may be sodium or potassium. The alkaline earth metal may be selected from the group consisting of magnesium and calcium. Also contemplated are mixed salts, which contain different metals, preferably a combination of two or more of the above metals. In the compounds of formula II, each Me may thus independently be selected from an alkali metal, alkaline earth metal, aluminum, lead or zinc. The alkali metal may be sodium or potassium and the alkaline earth metal may be selected from the group consisting of magnesium and calcium. If more than one Me ion are present in the salt, each Me can be the same or different.

In one embodiment of the invention, the metal salt is a sodium or calcium salt. In one specific embodiment of the invention, the metal salt is trisodium THEIC.

The stabilizer compositions according to the present invention can be added to the halogen-containing polymer in various amounts. In various embodiments, it can be added in an amount such that the metal salts of the compounds of formula I are added in an amount of from about 0.01 to about 20.0 part per 100 parts of resin ("per hundred of resin"=phr). In various embodiments, the metal salt compound can be added in an amount of from about 0.01 to about 10.0 parts per 100 parts of resin (phr). In one embodiment, the metal salt compound can be added in an amount of from about 0.1 to about 5.0 phr, for example in an amount of from about 0.5 to about 1.5 phr, for example about 0.5, 0.6, 0.7, 0.8, 0.9, 1.0, 1.1, 1.2, 1.3, 1.4 or 1.5 phr.

The stabilizer composition according to the present invention can be added in total in an amount of from about 0.01 to about 10.0 parts per 100 parts of resin (phr), preferably in an amount of from about 0.05 to about 8.0 phr, more preferably in an amount of from about 0.5 to about 5.0 phr.

The stabilizer composition can comprise additional (co-) stabilizers and/or other auxiliaries, as described below. These may be present in a ready-to-use formulation of the stabilizer composition or may be added separately to the polymer or the polymer mixture upon use.

In various embodiments, the stabilizer composition according to the invention can comprise one or more of the following additional additives, such as, for example, primary stabilizers, co-stabilizers, zeolites, antioxidants, fillers, plasticizers, dyestuffs, pigments, antistatic agents, surfactants, blowing agents, impact modifiers, UV stabilizers, lubricants, processing agents or the like.

Co-stabilizers are compounds which provide a further stabilizing contribution for halogen-containing polymers when used in the stabilizer composition according to the present invention. Possible co-stabilizers can be chosen from the group consisting of 1,3-diketone compounds, polyols, metal salts, natural or synthetic minerals, such as hydrotalcites, hydrocalumites and zeolites, amino acid derivatives, organic esters of phosphorous acid, epoxy compounds, salts of halogen-containing oxy acids, such as perchlorates, and EDTA.

Examples of 1,3-diketone compounds include, but are not limited thereto, dibenzoylmethane, stearoylbenzoyl-methane, palmitoylbenzoylmethane, myristoylbenzoyl-methane, lauroylbenzoylmethane, benzoylacetone, acetyl-acetone, tribenzoylmethane, diacetylacetobenzene, p-methoxystearoylacetophenone, acetoacetic acid esters and acetylacetone and metal salts thereof, in particular those of lithium, sodium, potassium, calcium, magnesium, titanium and/or aluminum.

Co-stabilizers from the group of polyols include, but are not limited thereto, glycerol, pentaerythritol, di- and tripentaerythritol, trismethylolpropane (TMP), di-TMP, sorbitol, sorbite, isosorbid, mannitol, malititol, saccharides, disaccharides (in particular sucrose, 4-O-[beta]-D-galactoyranosyl-D-glucose, 4-O-alpha-D-glucopyranosyl-D-glucose, 6-O-(6-deoxy-alpha-L-mannopyranosyl)-D-glucose, alpha-D-glucopyranosyl-alpha-D-gluco-pyranoside, 6-O-alpha-D-glucopyranosyl-D-glucose, 4-O-[beta]-D-glucopyranosyl-D-glucose, 2-O-[beta]-D-glucopyranosyl-D-glucose, 6-O-alpha-D-glucopyranosyl-D-glucitol, 3-O-alpha-D-glucopyranosyl-D-fructose, 6-O-[beta]-D-gluco-pyranosyl-D-glucose, 4-O-[beta]-D-galactopyranosyl-D-glucitol, 4-O-alpha-D-glucopyranosyl-D-glucitol, 6-O-alpha-D-galactopyranosyl-D-glucose, 3-O-alpha-D-galactopyranosyl-D-myo-inositol, 4-O-[beta]-D-galacto-pyranosyl-D-fructose, 4-O-[beta]-D-galactopyranosyl-[beta]-D-glucopyranose, 6-O-alpha-D-glucopyranosyl-D-fructose, 4-O-[beta]-D-galactopyranosyl-alpha-D-glucopyranose, 2-O-(6-deoxy-alpha-L-mannopyranosyl)-D-glucose, 4-O-alpha-D-glucopyranosyl-D-fructose, 2-O-[beta]-D-glucopyranosyl-alpha-D-glucopyranose, 1-O-alpha-D-glucopyranosyl-D-mannitol, 6-O-(6-deoxy-alpha-L-mannopyranosyl)-[beta]-D-glucopyranose, 2-O-[beta]-D-glucopyranosyl-[beta]-D-gluco-pyranose, 6-O-alpha-D-glucopyranosyl-alpha-6-gluco-pyranose, 2-O-alpha-D-glucopyranosyl-alpha-D-gluco-pyranose, 2-O-alpha-D-glucopyranosyl-[beta]-D-glucopyranose, 1-O-alpha-D-glucopyranosyl-D-fructose, 6-O-alpha-D-glucopyranosyl-alpha-D-fructofuranose, 6-O-alpha-D-glucopyranosyl-D-glucitol, 4-O-[beta]-D-galactopyranosyl-D-glucitol, 4-O-alpha-D-glucopyranosyl-D-glucitol, 1-O-alpha-D-glucopyranosyl-D-mannitol), trisaccharides, polysaccharides, in particular polyvinyl alcohols, starch, cellulose and partial esters thereof.

Exemplary salts of a halogen-containing oxy acid include inorganic or organic salts of perchloric acid. Examples of suitable inorganic perchlorates are those of the general formula $M(ClO_4)_k \cdot xH_2O$, wherein M is Li, Na, K, Mg, Ca, Sr, Zn, Al, La or Ce, k is depending on the valency of the metal 1, 2, 3 or 4 and x is 0 or an integer from 1 to 10.

Suitable organic perchlorates include the onium salts of perchlorates, as described below. In the context of the present invention, the term "onium salt" denotes a compound that is an ammonium, sulfonium or phosphonium salt. An "onium salt" in accordance with the present invention is an organic onium salt. That means that the ammonium, sulfonium or phosphonium group of the onium salt carries at least one organic radical. An onium salt may carry 1, 2, 3 or 4 organic radicals according to the nature of the onium salt. The organic radicals can be bonded to the onium radical, for example, by way of a C—X linkage, where X is S, N or P. It is equally possible, however, for the organic radicals to be bonded to the onium radical by way of a further hetero atom, for example an O atom.

Examples of co-stabilizers from the group of metal salts include, but are not limited thereto, hydroxides, oxides, carbonates, basic carbonates and carboxylic acid salts of alkali metals, alkaline earth metal, aluminum, lead, zinc, and titanium. The alkali and alkaline earth metals include lithium, sodium, potassium, magnesium and calcium. In one embodiment of the present invention, the metal salts can be salts of carboxylic acids, for example $C_2$-$C_{22}$-carboxylic acids, preferably higher carboxylic acids, such as, for example, stearic, palmitic, myristic, lauric, oleic, oleinic and ricinoleic acid.

In various embodiments of the invention, a stabilizer composition according to the invention comprises at least one basic calcium salt. Suitable basic calcium salts are, for example, calcium oxide, calcium carbonate and calcium hydroxide. The basic calcium salts may optionally have been surface-modified.

A stabilizer composition according to the invention can comprise the mentioned metal oxides, metal hydroxides or metal soaps, or a mixture of two or more thereof, in an amount of up to about 50% by weight, for example in an amount of up to about 30% by weight Examples of natural and synthetic minerals include, but are not limited thereto, A3-, A4-, A5-zeolites, zeolites of the mordenite, erionite, faujasite X or Y type and ZSM-5-zeolites, hydrotalcites (of the Alcamizer 1 and 4 type) and/or mixtures thereof. Further suitable hydrotalcites, zeolites and alkali alumocarbonates are described, for example, on pages 27 to 29 of EP-A 1 046 668, on pages 3, 5 and 7 of EP-A 256 872, on pages 2 and 3 of DE-C 41 06 411 or on pages 2 and 3 of DE-C 41 06 404. The hydrotalcites, zeolites and alkali alumocarbonates suitable as additives can be present in a stabilizer composition according to the invention in an amount of up to about 50% by weight, for example up to about 30% by weight.

Examples of co-stabilizers from the group of amino acid derivatives include, but are not limited thereto, glycine, alanine, lysine, tryptophan, acetylmethionine, pyrrolidonecarboxylic acid, [alpha]-aminocrotonic acid, [alpha]-aminoacrylic acid, [alpha]-aminoadipic acid, indol-, pyrimidine- and urea-derivatives and the like, and the corresponding esters thereof. The alcohol components of these esters can include monofunctional alcohols, such as, for example, methyl alcohol, ethyl alcohol, propyl alcohol, i-propyl alcohol, butyl alcohol, [alpha]-ethylhexanol, octyl alcohol, i-octyl alcohol, lauryl alcohol, stearyl alcohol and the like, and polyols, such as, for example, ethylene glycol, propylene glycol, 1,3-butanediol, 1,4-butanediol, glycerol, diglycerol, trismethylolpropane, pentaerythritol, dipentaerythritol, erythritol, sorbitol, mannitol and the like.

Examples of co-stabilizers from the group of esters of phosphorous acid include, but are not limited thereto, triaryl phosphites, such as, for example, triphenyl phosphite, tris(p-nonylphenyl) phosphite; alkyl aryl phosphites, such as, for example, monoalkyl diphenyl phosphites, e.g. diphenyl isooctyl phosphite, diphenyl isodecyl phosphite; and dialkyl monophenyl phosphites, such as, for example, phenyl diisooctyl phosphite, phenyl diisodecyl phosphite; and trialkyl phosphites, such as triisooctyl phosphite, tristearyl phosphite and the like.

Examples of co-stabilizers from the group of epoxy compounds include, but are not limited thereto, various animal and plant oils, such as, for example, epoxidised soybean oil, epoxidised olive oil, epoxidised linseed oil, epoxidised castor oil, epoxidised groundnut oil, epoxidised maize oil, epoxidised cottonseed oil, epoxidised-rape oil, epoxidized carboxylic acid esters, such as, for example, epoxidized epoxymethyl oleate, epoxybutyl oleate, epoxidized alicyclic compounds, glycidyl ethers, such as, for example, bisphenol A diglycidyl ether, bisphenol F diglycidyl ether; glycidyl esters, such as glycidyl acrylate, glycidyl methacrylate, their polymers, copolymers; and epoxidized polymers, such as epoxidized polybutadiene, epoxidized ABS, and the like. Further suitable epoxy compounds are described, for example, on pages 3 to 5 of EP-A 1 046 668.

Also suitable as additives in the context of the present invention are, for example, amino alcohols. Suitable amino alcohols in the context of the present invention are in principle any compounds having at least one OH group and a primary, secondary or tertiary amino group or a combination of two or more of the mentioned amino groups. Suitable amino alcohols are, for example, mono- or poly-hydroxy compounds which are based on linear or branched, saturated or unsaturated aliphatic mono- or poly-amines. There are suitable in this connection, for example, OH-group-carrying derivatives of primary mono- or poly-amino compounds having from 2 up to about 40, for example from 6 up to about 20, carbon atoms. Examples thereof are corresponding OH-group-carrying derivatives of ethylamine, n-propylamine, isopropylamine, n-propylamine, sec-propylamine, tert-butylamine, 1-aminoisobutane, and substituted amines having from 2 to about 20 carbon atoms, such as 2-(N,N-dimethylamino)-1-aminoethane. Suitable OH-group-carrying derivatives of diamines are, for example, those based on diamines having a molecular weight of from about 32 to about 200 g/mol, the corresponding diamines having at least two primary, two secondary, or one primary and one secondary amino group(s). Examples thereof are diaminoethane, the isomeric diaminopropanes, the isomeric diaminobutanes, the isomeric diaminohexanes, piperazine, 2,5-dimethyl-piperazine, amino-3-aminomethyl-3,5,5-trimethylcyclohexane (isophoronediamine, IPDA), 4,4'-diaminodicyclohexylmethane, 1,4-diaminocyclohexane, amino-ethylethanolamine, hydrazine, hydrazine hydrate or triamines, such as diethylenetriamine or 1,8-diamino-4-aminomethyloctane, triethylamine, tributylamine, dimethylbenzylamine, N-ethyl-, N-methyl-, N-cyclohexyl-morpholine, dimethylcyclohexylamine, dimorpholinodiethyl ether, 1,4-diazabicyclo[2.2.2]octane, 1-azabicyclo[3.3.0]octane, N,N,N',N'-tetramethylethylenediamine, N,N,N',N'-tetramethylbutanediamine, N,N,N',N'-tetramethyl-1,6-hexanediamine, pentamethyldiethylenetriamine, tetramethyldiaminoethyl ether, bis(dimethylaminopropyl)urea, N,N'-dimethylpiperazine, 1,2-dimethylimidazole or di(4-N,N-dimethylaminocyclohexyl)methane.

Especially suitable are aliphatic amino alcohols having from 2 to about 40, preferably from 6 to about 20, carbon atoms, for example 1-amino-3,3-dimethyl-pentan-5-ol, 2-aminohexane-2',2"-diethanolamine, 1-amino-2,5-dimethylcyclohexan-4-ol, 2-aminopropanol, 2-aminobutanol, 3-aminopropanol, 1-amino-2-propanol, 2-amino-2-methyl-1-propanol, 5-aminopentanol, 3-aminomethyl-3,5,5-trimethylcyclohexanol, 1-amino-1-cyclopentane-methanol, 2-amino-2-ethyl-1,3-propanediol, 2-(dimethylaminoethoxy)-ethanol, aromatic-aliphatic or aromatic-cycloaliphatic amino alcohols having from 6 to about 20 carbon atoms, there coming into consideration as aromatic structures heterocyclic or isocyclic ring systems such as naphthalene derivatives or, especially, benzene derivatives, such as 2-aminobenzyl alcohol, 3-(hydroxymethyl)aniline, 2-amino-3-phenyl-1-propanol, 2-amino-1-phenylethanol, 2-phenylglycinol or 2-amino-1-phenyl-1,3-propanediol, and also mixtures of two or more such compounds.

Within the scope of an especially preferred embodiment of the present invention, the amino alcohols used are heterocyclic compounds having a cyclic ring system containing amino groups, the OH groups being bonded to the ring either directly or preferably by way of spacers. Within the scope of an especially preferred embodiment of the present invention there are used heterocyclic amino alcohols that have at least 2, preferably at least 3, amino groups in the ring. As central ring component of the amino alcohols suitable for use according to the invention there are especially suitable the trimerisation products of isocyanates.

Special preference is given to hydroxyl-group-containing isocyanurates, in particular tris(hydroxymethyl)isocyanurate (THEIC).

Further suitable co-stabilizers include, but are not limited to 2-[2-[bis(carboxymethyl)amino]ethyl-(carboxymethyl)amino]acetic acid (EDTA), N,N'-ethylenediamine disuccinic acid, 2-[2-[2-[2-[bis(carboxymethyl)amino]ethoxy]ethoxy]ethyl-(carboxymethyl)amino]acetic acid, citric acid as well as salts or derivatives thereof.

Examples of antioxidants comprise, but are not limited thereto, alkylphenols, hydroxyphenyl propionates, hydroxybenzyl compounds, alkylidenebisphenols, thiobisphenols and aminophenols, in particular e.g. 2,6-di-tert-butyl-4-methylphenol, 2,6-dibenzyl-4-methylphenol, stearyl 3-(3'-5'-di-tert-butyl-4'-hydroxyphenyl)propionate, 4,4'-thiobis(3-methyl-6-tert-butylphenol), 4-nonylphenol, 2,2'-methylenebis(4-methyl-6-tert-butylphenol), 2,5-di-tert-butyl-hydroquinone, 4,4',4''-(1-thethyl-1-propenyl-3-ylidene)-tris[2-(1,1-dimethylethyl)-5-methylphenol], neutral or basic lithium, magnesium, calcium and aluminum salts thereof and sterically hindered amines and/or phosphonites and mixtures thereof.

Exemplary fillers include, but are not limited to chalk, dolomite, wollastonite, magnesium oxide, magnesium hydroxide, silicates, glass fibres, talc, kaolin, in pure or coated form, as well as carbon black or graphite, wood flour or other renewable raw materials.

Pigments that may be added to the stabilizer compositions of the invention include, but are not limited to titanium dioxide, in particular in its anatase and/or rutile modification form. Further examples of suitable inorganic pigments include, but are not limited to, carbon black, $Fe_2O_3$, $Sb_2O_3$, (Ba, Sb)$O_2$, $Cr_2O_3$, spinels, such as cobalt blue and cobalt green, Cd (S, Se) or ultramarine blue. Suitable organic pigments are, for example, azo pigments, phthalocyanine pigments, quinacridone pigments, perylene pigments, diketopyrrolopyrrole pigments or anthraquinone pigments.

Paraffin wax can be used, for example, as a lubricant. In one embodiment, the paraffin wax can be a mixture of alkanes with the general empirical formula $C_nH_{2n+2}$. n is an integer from 20 to 100. The mixture can comprise both straight-chain and branched-chain components, and also purely straight-chain components.

Other suitable lubricants include, but are not limited to, polyethylene waxes, polypropylene waxes, montan waxes, ester lubricants, such as fatty acid esters, purified or hydrogenated natural or synthetic triglycerides or partial esters, amide waxes, chloroparaffins, glycerol esters or alkaline earth soaps. Lubricants suitable for use are also described in "Kunststoffadditive", R. Gächter/H. Müller, Carl Hanser Verlag, 3rd edition, 1989, pages 478-488. Also suitable as lubricants are, for example, fatty ketones, as described in DE 4,204,887, and also silicone-based lubricants, as mentioned, for example, in EP-A 0 259 783, or combinations thereof, as mentioned in EP-A 0 259 783. A stabilizer composition according to the invention can comprise the described lubricants in an amount of from 0 up to about 70% by weight, especially up to about 40% by weight Fillers can be used in an amount of from approximately 0 to approximately 100 phr or from approximately 1 to approximately 50 phr. In one embodiment of the present invention, fillers can be used in an amount of from approximately 2 to approximately 20 phr. Plasticizers can be used in an amount of from approximately 0 to approximately 100 phr, for example from approximately 0.05 to approximately 50 phr. Lubricants can be used in an amount of from approximately 0.05 to approximately 3 phr, for example from approximately 0.1 to approximately 2 phr.

The co-stabilizers described above can be used in identical amounts to the lubricants.

Blowing agents suitable for use in the compositions of the invention include, but are not limited to organic azo and hydrazo compounds, tetrazoles, oxazines, isatoic anhydride, salts of citric acid, for example ammonium citrate, and also sodium carbonate and sodium hydrogen carbonate. Especially suitable are, for example, ammonium citrate, azodicarbonamide or sodium hydrogen carbonate or mixtures of two or more thereof. Also suitable are physical blowing agents, such as liquids that pass into the gaseous state when the temperature is suitably increased or gases, for example water, $CO_2$ (supercritical), air or inert gases such as hydrogen, helium, argon or the like.

Within the scope of a preferred embodiment of the present invention, a stabilizer composition according to the invention comprises at least one blowing agent. The proportion of blowing agents in a stabilizer composition according to the invention is preferably from about 0.01 to about 20% by weight, for example from about 0.1 to about 10% by weight or from about 0.5 to about 5% by weight.

Suitable as plasticisers are, for example, compounds from the group of phthalic acid esters, such as di-2-ethylhexyl, di-n-octyl, diisooctyl, diisononyl, diisodecyl, dicyclohexyl, dimethylcyclohexyl, dimethyl glycol, dibutyl glycol, benzylbutyl or diphenyl phthalate and also mixtures of phthalates, for example mixtures of alkyl phthalates having from 7 to 9 or 9 to 11 carbon atoms in the ester alcohol or mixtures of alkyl phthalates having from 6 to 10 and 8 to 10 carbon atoms in the ester alcohol. Especially suitable in the sense of the present invention are di-2-ethylhexyl, di-n-octyl, diisooctyl, diisononyl, diisodecyl, diisotridecyl and benzylbutyl phthalate and also the mentioned mixtures of alkyl phthalates.

Also suitable as plasticisers are the esters of aliphatic dicarboxylic acids, especially the esters of adipic, azelaic or sebacic acid or mixtures of two or more thereof. Examples of such plasticisers are di-2-ethylhexyl adipate, diisooctyl adipate, diisononyl adipate, diisodecyl adipate, benzylbutyl adipate, benzyloctyl adipate, di-2-ethylhexyl azelate, di-2-ethylhexyl sebacate and diisodecyl sebacate. Further suitable are trimellitic acid esters, such as tri-2-ethylhexyl trimellitate, triisotridecyl trimellitate, triisooctyl trimellitate and also trimellitic acid esters having from 6 to 8, 6 to 10, 7 to 9 or 9 to 11 carbon atoms in the ester group or mixtures of two or more of the mentioned compounds.

Additional suitable plasticisers are known to those skilled in the art, and include, by way of example only, phosphoric acid esters including tributyl phosphate, tri-2-ethylbutyl phosphate, tri-2-ethylhexyl phosphate, trichloroethyl phosphate, 2-ethyl-hexyl-di-phenyl phosphate, triphenyl phosphate, tricresyl phosphate or trixylenyl phosphate, or mixtures of two or more thereof, chlorinated hydrocarbons (paraffins) or hydrocarbons.

A stabilizer composition according to the invention can comprise the described plasticisers in an amount of from 0 up to about 99.5% by weight, especially up to about 30% by weight, up to about 20% by weight or up to about 10% by weight. Within the scope of a preferred embodiment of the present invention, the lower limit for the described plasticisers as constituent of the stabilizer compositions according to the invention is about 0.1% by weight or more, for example about 0.5% by weight, 1% by weight, 2% by weight or 5% by weight.

A stabilizer composition according to the invention may, for example, comprise only one of the metal salts of the compounds of formula I. In the context of the present invention it is however also contemplated that the stabilizer composition according to the invention comprises a mixture of two or more of the above-mentioned metal salt compounds. It may be a mixture of two or more different types of salts.

Similarly, the stabilizer composition of the invention may comprise one or more of the above described additives, including one or more of the same type of additives or compound.

In specific embodiments of the invention, the metal salt compound or a mixture of two or more such salts is finely distributed in the stabilizer composition. The term "finely distributed", as used in this context, means that discrete particles of the salt or of a mixture of two or more such salts, insofar as being present or identifiable at all, do not exceed an average particle size of 10 μm, 5 μm or 1 μm. Customary methods, such as light microscopy or electron microscopy, can be used for determining the particle size.

In various embodiments, less than 10% by weight of the metal salts of the compounds of formula I are in crystalline form with crystallites of a size of 30 μm or more, 20 μm or more, or 10 μm or more. The crystallite sizes can in principle be determined by any methods of determining particle sizes. Methods that are suitable in principle include, for example, screening methods, sedimentation methods and methods based on the diffraction or refraction of electromagnetic waves, especially of light. Also suitable are electron microscopic methods, such as scanning electron microscopy or transmission electron microscopy.

The proportion of metal salts of a compound of formula I or of a mixture of two or more of these metal salts in the stabilizer composition according to the invention is in total from about 0.1 to 100% by weight, from about 1 to 75% by weight, from about 2 to 50% by weight, or from about 3 to about 25% by weight of the stabilizer composition.

The stabilizer compositions of the invention can comprise, consist essentially of or consist of the above-described components.

In order to process halogen-containing polymers with the stabilizer composition according to the invention, the processes known from the prior art can be used. Examples of such processes include, but are not limited thereto, calendering, extrusion, injection molding, blow molding and the like.

The stabilizer compositions according to the invention can in principle be prepared in their simplest form by reacting an iso(thio)cyanuric acid or derivative thereof of formula I or a tautomer or stereoisomer thereof, as defined above, with a metal salt, for example a metal hydroxide or metal oxide. The reaction may be carried out in the presence of a catalyst, such as water. If water is used as a catalyst, only catalytic amounts of water are used.

In various embodiments, the metal hydroxide or metal oxide is selected from the group consisting of alkali metal hydroxides, alkaline earth metal hydroxides, alkaline earth metal oxides, aluminum hydroxide, lead hydroxide, lead oxide, zinc oxide, and zinc hydroxide. The alkali metal hydroxides can for example be sodium hydroxide or potassium hydroxide. The alkaline earth metal oxides or hydroxides include, but are not limited to, calcium oxide and calcium hydroxide. All metal salts may be used in form of suspensions, in particular aqueous suspensions.

"Reacting", as used in connection to the claimed process, includes simply mixing the educts in the presence of a catalyst. The reacting step may be carried out in a suitable non-aqueous solvent. Suitable solvents are preferably those that can be removed again after the reaction, optionally by heating of the mixture or by the application of reduced pressure or by a combination of the two measures. As the reaction produces water, the process can optionally include a step of removing the water once the reaction is finished or even during the reaction. This step may, for example, be a simple drying step at elevated temperature and/or at reduced pressure.

The reaction of the two educts can be effected in principle in any desired way, preferably sufficient intermixing of the two should be ensured.

The process according to the invention can also be carried out, for example, as a combination of mixing and grinding processes. In that case, for example during the grinding of the compound of formula I or a mixture of two or more such compounds, an aqueous solution/suspension of the metal oxide or hydroxide can be supplied in the context of the grinding operation.

When a stabilizer composition according to the invention is to comprise one or more additives in addition to the metal salt of the compound of formula I, those additives can be added before, during or after the reaction. Addition of additives before or during the mixing should take place, however, only when the additives are inert towards the compounds being mixed. Otherwise, namely when the additives are not inert, they are added (where the stabilizer composition according to the invention is to comprise such additives) only after the reaction.

In one specific embodiment of the process for the formation of the metal salts of the compounds of formula I, the iso(thio)cyanuric acid or derivative thereof of formula I is mixed with a metal hydroxide or metal oxide, some drops of water are added as a catalyst and the reaction mixture is heavily stirred in a mixer. After the exothermic reaction is completed or during this reaction the water, which forms by the reaction, is removed, for example by drying.

The resulting metal salts of iso(thio)cyanuric acid or derivatives thereof can be milled and then used as ingredients for stabilizer systems for halogenated thermoplastics.

The invention also encompasses the product obtained by the above-described process.

The stabilizer compositions according to the invention are suitable for the stabilization of halogen-containing polymers. The present invention therefore relates also to a polymer composition comprising a halogen-containing polymer or a mixture of two or more halogen-containing polymers and a stabilizer composition according to the invention.

Examples of such halogen-containing polymers are polymers of vinyl chloride, vinyl resins containing vinyl chloride units in the polymer backbone, copolymers of vinyl chloride and vinyl esters of aliphatic acids, especially vinyl acetate, copolymers of vinyl chloride with esters of acrylic and methacrylic acid or acrylonitrile or mixtures of two or more thereof, copolymers of vinyl chloride with diene compounds or unsaturated dicarboxylic acids or anhydrides thereof, for example copolymers of vinyl chloride with diethyl maleate, diethyl fumarate or maleic anhydride, post-chlorinated polymers and copolymers of vinyl chloride, copolymers of vinyl chloride and vinylidene chloride with unsaturated aldehydes, ketones and other compounds such as acrolein, crotonaldehyde, vinyl methyl ketone, vinyl methyl ether, vinyl isobutyl ether and the like, polymers and copolymers of vinylidene chloride with vinyl chloride and other polymerisable compounds, such as those already mentioned above, polymers of vinyl chloroacetate and dichlorodivinyl ether, chlorinated polymers of vinyl acetate, chlorinated polymeric esters of acrylic acid and [alpha]-substituted acrylic acids, chlorinated polystyrenes, for example polydichlorostyrene, chlorinated polymers of ethylene, polymers and post-chlorinated polymers of chlorobutadiene and copolymers thereof with vinyl chloride and also mixtures of two or more of the mentioned polymers or polymer mixtures that contain one or more of the above-mentioned polymers. Within the scope of a preferred embodiment of the present invention, the stabilizer compositions according to the invention are used for the production of moulded articles of PVC-U, such as window profiles, industrial profiles, tubes and plates.

Also suitable for stabilization with the stabilizer compositions according to the invention are the graft polymers of PVC with EVA, ABS or MBS. Preferred substrates for such graft copolymers are also the afore-mentioned homo- and co-polymers, especially mixtures of vinyl chloride homopolymers with other thermoplastic or elastomeric polymers, especially blends with ABS, MBS, NBR, SAN, EVA, CPE; MBAS, PM (polyalkyl acrylate), PAMA (polyalkyl methacrylate, especially PMMA-polymethyl methacrylate), EPDM, polyamides or polylactones.

Likewise suitable for stabilization with the stabilizer compositions according to the invention are mixtures of halogenated and non-halogenated polymers, for example mixtures of the above-mentioned non-halogenated polymers with PVC, especially mixtures of polyurethanes and PVC.

Furthermore, it is also possible for recyclates of chlorine-containing polymers to be stabilized with the stabilizer compositions according to the invention, in principle any recyclates of the above-mentioned halogenated polymers being suitable for this purpose. PVC recyclate, for example, is suitable in the context of the present invention.

Within the scope of a preferred embodiment of the present invention, a polymer composition according to the invention comprises the stabilizer composition according to the invention in an amount of from 0.1 to 20 phr, especially from approximately 0.5 to approximately 15 phr or from approximately 1 to approximately 12 phr. The unit phr represents "per hundred resin" and thus relates to parts by weight per 100 parts by weight of polymer.

A polymer composition according to the invention preferably comprises as halogenated polymer at least a proportion of PVC, the PVC content being especially at least about 20% by weight, preferably at least about 50% by weight, for example at least about 80% by weight or at least about 90% by weight.

The polymer compositions of the invention can additionally comprise one or more of the additives described above in relation to the stabilizer compositions. These additives can be added to the polymer composition as part of the stabilizer composition or separately in any desired order, i.e. before, simultaneously with or after addition of the stabilizer composition.

The present invention relates also to a method of stabilizing halogen-containing polymers in which a halogen-containing polymer or a mixture of two or more halogen-containing polymers or a mixture of one or more halogen-containing polymers and one or more halogen-free polymers is contacted, for example mixed, with a stabilizer composition according to the invention.

Similarly, the invention also concerns the use of a stabilizer composition according to the invention for stabilizing halogen-containing polymers.

The mixing together of polymer or polymers and the stabilizer composition according to the invention can in principle be effected at any time before or during the processing of the polymer. For example, the stabilizer composition can be mixed into the powdery or granular polymer prior to processing. It is equally possible, however, to add the stabilizer composition to the polymer or polymers in the softened or molten state, for example during processing in an extruder, in the form of an emulsion or dispersion, in the form of a pasty mixture or in the form of a dry mixture.

A polymer composition according to the invention can be brought into a desired form in known manner. Suitable methods are, for example, calendering, extrusion, injection-molding, sintering, extrusion blowing or the plastisol process. A polymer composition according to the invention can also be used, for example, in the production of foamed materials. In principle, the polymer compositions according to the invention are suitable for the production of hard or soft PVC, including for the production of PVC foams.

A polymer composition according to the invention can be processed to form molded articles. The present invention therefore relates also to molded articles comprising a stabilizer composition according to the invention or a polymer composition according to the invention or consisting of a polymer composition according to the invention.

The term "molded article" in the context of the present invention in principle includes any three-dimensional structures that can be produced from a polymer composition according to the invention. In the context of the present invention the term "molded article" includes, for example, wire sheathings, automobile components, for example automobile components such as are used in the interior of the automobile, in the engine space or on the outer surfaces, cable insulations, decorative films, agricultural films, hoses, shaped sealing elements, office films, hollow bodies (bottles), packaging films (deep-draw films), blown films, tubes, pipes, foamed materials, heavy duty profiles (window frames), light wall profiles, structural profiles, sidings, fittings, plates, foamed panels, co-extrudates having a recycled core, or housings for electrical apparatus or machinery, for example computers or household appliances.

Further examples of molded articles that can be produced from a polymer composition according to the invention are synthetic leather, floor coverings, textile coatings, wall coverings, coil coatings and underseals for motor vehicles.

The citing or discussion of a previously published document in this application should not necessarily be taken as an acknowledgement that the document is part of the state of the art or is common general knowledge. All documents listed are hereby incorporated herein by reference in their entirety.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognise that the invention is also thereby described in terms of any individual member or subgroup of members of the Markush group. The invention is illustrated in more detail by the following examples, but without being limited thereto

EXAMPLES

Dynamic stability was tested by applying powder mixtures into a Brabender laboratory compounder. The compounder ran with 80 RPM at 180° C. The powder mixture melted and plastificated after around 2 minutes. Starting after 4 minutes, aliquot samples were removed at the time points given in the tables and the Yellowness Index of these specimens was determined by a Minolta CM 2002 spectrophotometer and calculated according to ASTM D1925.

Example 1

Mixtures of ingredients in Table 1 were prepared by hand and applied to a Brabender laboratory compounder for monitoring the dynamic stability. Formulation 1 is a comparative formulation while formulations 2 and 3 are according to the invention.

TABLE 1

Ingredients of formulations 1, 2 and 3 (in parts per weight)

| Ingredients | Form. 1 | Form. 2 | Form. 3 |
|---|---|---|---|
| PVC K57 | 100.00 | 100.00 | 100.00 |
| Filler | 4.56 | 4.56 | 4.56 |
| Acrylic Modifier | 2.20 | 2.20 | 2.20 |
| TiO2 | 2.00 | 2.00 | 2.00 |
| Hydrogenated Castor Oil | 0.73 | 0.73 | 0.73 |
| Calcium Stearate | 0.23 | 0.23 | 0.23 |
| Paraffin Wax | 0.30 | 0.30 | 0.30 |
| PE Wax | 0.14 | 0.14 | 0.14 |
| Ca-Acetylacetone | 0.24 | 0.24 | 0.24 |
| THEIC | 0.24 | 0.24 | 0.24 |
| Stearoyl benzoyl methane (Rhodiastab 50) | 0.12 | 0.12 | 0.12 |
| Antioxidant (hindered Phenol) | 0.18 | 0.18 | 0.18 |
| Zinc Laurate | 0.94 | 0.94 | 0.74 |
| Zinc Stearate | | | 0.20 |
| Trisodium THEIC | | 0.85 | 0.85 |
| | 111.88 | 112.73 | 112.73 |
| L | 89.92 | 89.8 | 89.62 |
| a | −0.94 | −1.28 | −1.13 |
| b | 6.16 | 7.54 | 6.98 |

The difference of Formulation 2 and 3 is the combination of Zn-containing soaps. Both formulations 2 and 3 perform much better in dynamic stability than the reference.

TABLE 2

Yellowness Index YI

| YI | Form. 1 | Form. 2 | Form. 3 |
|---|---|---|---|
| 4 min | 10.9 | 14.7 | 13.5 |
| 6 min | 17.7 | 17.3 | 19.4 |
| 8 min | degr. | 25.3 | 27.6 |
| 10 min | | 42.7 | 44.3 |
| 12 min | | degr. | degr. |

Example 2

Mixtures of the ingredients of Table 3 were prepared by hand. Formulations 4, 6, 7 and 9 are comparative formulations, while Formulations 5 and 8 are according to the invention.

TABLE 3

Ingredients of formulations 4 to 9 (in parts per weight)

| Ingredients | Form. 4 | Form. 5 | Form. 6 | Form. 7 | Form. 8 | Form. 9 |
|---|---|---|---|---|---|---|
| PVC K57 | 100.00 | 100.00 | 100.00 | 100.00 | 100.00 | 100.00 |
| Filler | 10.00 | 10.00 | 10.00 | 10.00 | 10.00 | 10.00 |
| Processing Aid | 2.00 | 2.00 | 2.00 | 2.00 | 2.00 | 2.00 |
| TiO2 | 2.00 | 2.00 | 2.00 | 2.00 | 2.00 | 2.00 |
| Ca-Stearate | 1.07 | 1.07 | 1.07 | 1.07 | 1.07 | 1.07 |
| PE-Wax | 0.22 | 0.22 | 0.22 | 0.22 | 0.22 | 0.22 |
| ox PE-Wax (AC 316 A) | 0.11 | 0.11 | 0.11 | 0.11 | 0.11 | 0.11 |
| EVA Copolymer (AC 400 A) | 0.11 | 0.11 | 0.11 | 0.11 | 0.11 | 0.11 |
| Hydrogenated Castor Oil | 0.65 | 0.65 | 0.65 | 0.65 | 0.65 | 0.65 |
| Stearyl stearate | 0.20 | 0.20 | 0.20 | 0.20 | 0.20 | 0.20 |
| THEIC | | | 1.00 | | | 1.00 |
| Antioxidant | 0.10 | 0.10 | 0.10 | 0.10 | 0.10 | 0.10 |
| Uracil (DMAU) | 0.20 | 0.20 | 0.20 | 0.20 | 0.20 | 0.20 |
| Sodium perchlorate | | | | 0.06 | 0.06 | 0.06 |
| Trisodium THEIC | | 1.00 | | | 1.00 | |
| L | 90.21 | 87.34 | 90.12 | 90.15 | 90.25 | 89.78 |
| a | −1.28 | −1.18 | −0.81 | −1.24 | −1.22 | −0.84 |
| b | 3.76 | 3.07 | 2.57 | 3.71 | 3.37 | 2.67 |

TABLE 4

Further Formulations

| Ingredients | Form. 10 | Form. 11 | Form. 12 | Form. 13 | Form. 14 |
|---|---|---|---|---|---|
| PVC K57 | 100.00 | 100.00 | 100.00 | 100.00 | 100.00 |
| Filler | 10.00 | 10.00 | 10.00 | 10.00 | 10.00 |
| Processing Aid | 2.00 | 2.00 | 2.00 | 2.00 | 2.00 |
| TiO2 | 2.00 | 2.00 | 2.00 | 2.00 | 2.00 |
| Ca-Stearate | 1.07 | 1.07 | 1.07 | 1.07 | 1.07 |
| PE-Wax | 0.22 | 0.22 | 0.22 | 0.22 | 0.22 |
| ox PE-Wax (AC 316 A) | 0.11 | 0.11 | 0.11 | 0.11 | 0.11 |
| EVA Copolymer (AC 400 A) | 0.11 | 0.11 | 0.11 | 0.11 | 0.11 |
| Hydrogenated Castor Oil | 0.65 | 0.65 | 0.65 | 0.65 | 0.65 |
| Stearyl stearate | 0.20 | 0.20 | 0.20 | 0.20 | 0.20 |
| Trisodium Cyanurate |  | 1.00 | 1.00 | 1.00 |  |
| Tod 1076 |  |  | 0.10 | 0.10 |  |
| Uracil (DMAU) |  | 0.20 | 0.20 | 0.20 |  |
| Sodium perchlorate 55% solution |  |  | 0.10 | 0.10 |  |
| L | 77.77 | 87.34 | 89.81 | 90.1 | 77.89 |
| a | 9.05 | −1.18 | −1.17 | −1.23 | 9.03 |
| b | 15.13 | 3.07 | 3.32 | 3.43 | 15.08 |

The resulting dynamic stabilities are shown in table 5. It is obvious that the formulations according to the invention have a better color stability over the heating time and shear stress.

TABLE 5

Yellowness Index YI

| YI | Form. 4 | Form. 5 | Form. 6 | Form. 7 | Form. 8 | Form. 9 |
|---|---|---|---|---|---|---|
| 4 min | 9.02 | 9.55 | 4.65 | 9.17 | 9.37 | 5.11 |
| 8 min | 32.58 | 21.91 | 22.16 | 27.69 | 20.16 | 21.44 |
| 12 min | 61.19 | 41.98 | 65.77 | 60.29 | 36.56 | 51.56 |
| 16 min | 71.22 | 77.58 | 85.75 | 67.82 | 55.90 | 79.59 |
| 20 min | 67.36 | 91.50 | 41.17 | degr. | 73.09 | 76.04 |
| 24 min | degr. | 82.06 | degr. |  | 77.11 | 77.20 |
| 28 min |  | degr. |  |  | 73.42 | degr. |

Example 3

Table 6 shows Formulations 15 to 20, where Formulation 16 and 19 were according to the invention. The ingredient amounts in Table 6 are expressed in parts by weight per 100 parts by weight of PVC (phr), as in the examples before.

TABLE 6

Ingredients of Formulations 15 to 20 (in parts per weight)

| Ingredients | Form. 15 | Form. 16 | Form. 17 | Form. 18 | Form. 19 | Form. 20 |
|---|---|---|---|---|---|---|
| PVC K57 | 100.00 | 100.00 | 100.00 | 100.00 | 100.00 | 100.00 |
| Filler | 10.00 | 10.00 | 10.00 | 10.00 | 10.00 | 10.00 |
| Processing Aid | 2.00 | 2.00 | 2.00 | 2.00 | 2.00 | 2.00 |
| TiO2 | 2.00 | 2.00 | 2.00 | 2.00 | 2.00 | 2.00 |
| Hydrgen. Castor Oil | 0.70 | 0.70 | 0.70 | 0.70 | 0.70 | 0.70 |
| Ca Stearate | 0.20 | 0.20 | 0.20 | 0.20 | 0.20 | 0.20 |
| Zn Laurate | 1.00 | 1.00 | 1.00 | 1.00 | 1.00 | 1.00 |
| Paraffin Wax | 0.30 | 0.30 | 0.30 | 0.30 | 0.30 | 0.30 |
| PE Wax | 0.15 | 0.15 | 0.15 | 0.15 | 0.15 | 0.15 |
| Ca-Acetylacetone |  |  |  | 0.20 | 0.20 | 0.20 |
| Antioxidant | 0.10 | 0.10 | 0.10 | 0.10 | 0.10 | 0.10 |
| Stearoyl benzoyl methane | 0.10 | 0.10 | 0.10 | 0.10 | 0.10 | 0.10 |
| THEIC |  |  | 1.00 | 0.20 | 0.20 | 1.20 |
| Trisodium THEIC |  | 1.00 |  |  | 1.00 |  |
| L | 89.89 | 88.18 | 90.39 | 90.94 | 90.7 | 90.98 |
| a | −0.83 | −0.96 | −0.9 | −0.64 | −0.9 | −0.63 |
| b | 5.05 | 7.48 | 3.62 | 2.93 | 4.27 | 3 |

TABLE 7

Further Formulations

| Ingredients | Form. 21 | Form. 22 | Form. 23 | Form. 24 |
|---|---|---|---|---|
| PVC K57 | 100.00 | 100.00 | 100.00 | 100.00 |
| Filler | 10.00 | 10.00 | 10.00 | 10.00 |
| Processing Aid | 2.00 | 2.00 | 2.00 | 2.00 |
| TiO2 | 2.00 | 2.00 | 2.00 | 2.00 |
| Hydrgen. Castor Oil | 0.70 | 0.70 | 0.70 | 0.70 |
| Ca Stearate | 0.20 | 0.20 | 0.20 | 0.20 |
| Zn Laurate | 1.00 | 1.00 | 1.00 | 1.00 |
| 165 wax | 0.30 | 0.30 | 0.30 | 0.30 |
| PE-Wax | 0.15 | 0.15 | 0.15 | 0.15 |
| Trisodium Cyanurate |  |  | 1.00 | 1.00 |
| Antioxidant (1076) |  |  | 0.10 | 0.10 |
| Beta-Diketone (StBM) |  |  | 0.10 | 0.10 |
| Polyol (THEIC) |  |  | 0.20 | 0.20 |
| CaAcAc |  |  |  | 0.20 |
| L | 85.85 | 85.71 | 89.76 | 90.78 |
| a | −0.49 | −0.49 | −1.48 | −0.9 |
| b | 8 | 8.02 | 9.53 | 4.23 |

Table 8 shows the Yellowness Indices up to 12 minutes and it is obvious that the formulations containing the metal salt of isocyanuric acid—in this case tri sodium isocyanurate—shows a better colour hold than comparative formulations, even the ones containing the pure isocyanurate THEIC.

TABLE 8

| YI | Form. 10 | Form. 11 | Form. 12 | Form. 13 | Form. 14 | Form. 15 |
|---|---|---|---|---|---|---|
| | Yellowness Index YI | | | | | |
| 4 min | 4.26 | 0.85 | 1.33 | 1.33 | 2.50 | 2.43 |
| 8 min | degr. | 14.09 | 11.57 | 11.57 | 7.98 | 27.59 |
| 12 min | | 24.14 | 44.72 | 44.72 | 27.69 | degr. |

The invention claimed is:

1. A stabilizer composition for halogen-containing polymers, comprising at least one metal salt of a compound of formula I or stereoisomer thereof:

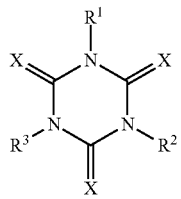

Formula I wherein
$R^1$, $R^2$ and $R^3$ are independently hydroxyethyl or 2,3-epoxypropanyl; and
X is O.

2. The stabilizer composition of claim 1, wherein the metal salt of the compound of formula I is a compound of formula II:

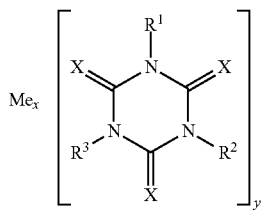

Formula II wherein
Me is a metal ion, x is an integer from 1 to 6, and y is an integer from 1 to 4.

3. The stabilizer composition of claim 1, wherein the metal is an alkali metal, alkaline earth metal, aluminum, lead or zinc.

4. The stabilizer composition of claim 3, wherein the alkali metal or alkaline earth metal is selected from the group consisting of sodium, potassium, magnesium and calcium.

5. The stabilizer composition of claim 4, wherein the isocyanuric acid metal salt is trisodium trishydroxyethylene isocyanurate.

6. The stabilizer composition of claim 1, further comprising one or more additional components selected from the group consisting of primary stabilizers, co-stabilizers, zeolites, antioxidants, fillers, plasticizers, dyestuffs, pigments, antistatic agents, surfactants, blowing agents, impact modifiers, UV stabilizers, lubricants, processing agents and other auxiliaries.

7. The stabilizer composition of claim 6, wherein the primary stabilizers or co-stabilizers are selected from the group consisting of 1,3-diketone compounds, polyols, metal salts, natural or synthetic minerals, amino acid derivatives, organic esters of phosphorous acid, epoxy compounds, salts of halogen-containing oxy acids and amino alcohols.

8. A process of preparing a stabilizer composition according to claim 1, comprising: reacting a compound of formula I or stereoisomer thereof:

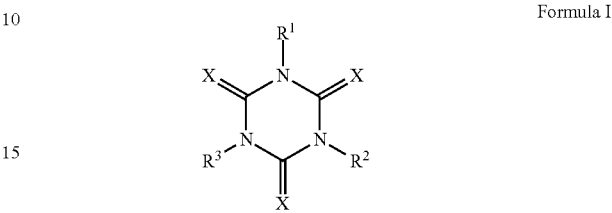

Formula I wherein
$R^1$, $R^2$ and $R^3$ are independently hydroxyethyl or 2,3-epoxypropanyl and
X is O;
with a metal hydroxide or metal oxide, wherein the reaction is carried out in the presence of water as a catalyst.

9. The process of claim 8, wherein the metal hydroxide or metal oxide is selected from the group consisting of alkali metal hydroxides, alkaline earth metal hydroxides, aluminum hydroxide, lead hydroxide, lead oxide, zinc oxide, and zinc hydroxide.

10. The process of claim 8, further comprising the step of drying the reaction product.

11. The process of claim 8, further comprising adding one or more additional components selected from the group consisting of primary stabilizers, co-stabilizers, zeolites, antioxidants, fillers, plasticizers, dyestuffs, pigments, antistatic agents, surfactants, blowing agents, impact modifiers, UV stabilizers, lubricants, processing agents and other auxiliaries to said composition before, during or after the reaction step.

12. A stabilizer composition obtainable by the process of claim 8.

13. A polymer composition comprising a halogen-containing polymer and a stabilizer composition of claim 1.

14. The polymer composition of claim 13, wherein the halogen-containing polymer is a thermoplastic.

15. The polymer composition of claim 14, wherein the thermoplastic is polyvinylchloride.

16. The polymer composition of claim 13, further comprising one or more additional components selected from the group consisting of primary stabilizers, co-stabilizers, zeolites, antioxidants, fillers, plasticizers, dyestuffs, pigments, antistatic agents, surfactants, blowing agents, impact modifiers, UV stabilizers, lubricants, processing agents and other auxiliaries.

17. The polymer composition of claim 13, wherein the amount of stabilizer composition in the polymer composition is from about 1 to 20 per hundred halogen-containing polymer resin (phr).

18. A molded article comprising or consisting of the polymer composition of claim 13.

19. A method for the stabilization of halogen-containing polymers, comprising contacting the halogen-containing polymer with a stabilizer composition according to claim 1.

20. The method according to claim 19, wherein the halogen-containing polymer is polyvinylchloride.

* * * * *